US00PP22043P2

(12) United States Plant Patent
Geibel

(10) Patent No.: US PP22,043 P2
(45) Date of Patent: Jul. 26, 2011

(54) GERANIUM PLANT NAMED 'PACSHORG'

(50) Latin Name: *Pelargonium×hortorum*
Varietal Denomination: Pacshorg

(75) Inventor: Martin Geibel, Dresden (DE)

(73) Assignee: Elsner PAC Jungpflanzen GbR, Dresden (DE)

( * ) Notice: Subject to any disclaimer, the term of this patent is extended or adjusted under 35 U.S.C. 154(b) by 0 days.

(21) Appl. No.: 12/655,603

(22) Filed: Dec. 31, 2009

(51) Int. Cl.
*A01H 5/00* (2006.01)

(52) U.S. Cl. ..... Plt./327

(58) Field of Classification Search ..... Plt./327
See application file for complete search history.

*Primary Examiner* — Susan B McCormick Ewoldt
(74) *Attorney, Agent, or Firm* — C. A. Whealy

(57) ABSTRACT

A new and distinct cultivar of Zonal Geranium plant named 'Pacshorg', characterized by its compact, upright and rounded plant habit; freely branching habit; vigorous growth habit; dark green-colored leaves; freely flowering habit; long flowering period; semi-double bright orange-colored flowers; and good garden performance.

1 Drawing Sheet

Botanical designation: *Pelargonium×hortorum*.
Cultivar denomination: 'PACSHORG'.

BACKGROUND OF THE INVENTION

The present invention relates to a new and distinct cultivar of Zonal Geranium plant, botanically known as *Pelargonium×hortorum,* and hereinafter referred to by the name 'Pacshorg'.

The new Zonal Geranium plant is a product of a planned breeding program conducted by the Inventor in Dresden, Germany. The objective of the breeding program is to create new uniform semi-double flowered Zonal Geranium plants with dark green-colored leaves and attractive flower coloration.

The new Zonal Geranium plant originated from a cross-pollination made by the Inventor in Dresden, Germany during the summer of 2005 of two unnamed proprietary selections of *Pelargonium×hortorum,* not patented. The new Zonal Geranium plant was discovered and selected by the Inventor as a single flowering plant from within the progeny of the stated cross-pollination in a controlled greenhouse environment in Dresden, Germany in June, 2006.

Asexual reproduction of the new Zonal Geranium plant by vegetative terminal cuttings in a controlled greenhouse environment in Dresden, Germany since January, 2007, has shown that the unique features of this new Zonal Geranium plant are stable and reproduced true to type in successive generations.

SUMMARY OF THE INVENTION

Plants of the new Zonal Geranium have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Pacshorg'. These characteristics in combination distinguish 'Pacshorg' as a new and distinct cultivar of Zonal Geranium:

1. Compact, upright and rounded plant habit.
2. Freely branching habit.

3. Vigorous growth habit.
4. Dark green-colored leaves.
5. Freely flowering habit.
6. Long flowering period.
7. Semi-double bright orange-colored flowers.
8. Good garden performance.

Plants of the new Zonal Geranium differ primarily from plants of the parent selections in plant vigor and flower color.

Plants of the new Zonal Geranium can be compared to plants of *Pelargonium×hortorum* 'Drapin', disclosed in U.S. Plant Pat. No. 10,561. In side-by-side comparisons conducted in Dresden, Germany, plants of the new Zonal Geranium differed from plants of 'Drapin' in the following characteristics:

1. Plants of the new Zonal Geranium were more compact than plants of 'Drapin'.
2. Plants of the new Zonal Geranium had larger flowers than plants of 'Drapin'.
3. Plants of the new Zonal Geranium had fewer flowers per umbel than plants of 'Drapin'.
4. Plants of the new Zonal Geranium and 'Drapin' differed in flower color.

BRIEF DESCRIPTION OF THE PHOTOGRAPH

The accompanying colored photograph illustrates the overall appearance of the new Zonal Geranium plant, showing the colors as true as it is reasonably possible to obtain in colored reproductions of this type. Colors in the photograph may differ slightly from the color values cited in the detailed botanical description which accurately describe the colors of the new Zonal Geranium plant. The photograph comprises a side perspective view of a typical flowering plant of 'Pacshorg' grown in a container.

DETAILED BOTANICAL DESCRIPTION

The aforementioned photograph and following observations, measurements and values describe plants grown in 19-cm containers in Dresden, Germany in a glass-covered greenhouse during the summer and autumn and under conditions which closely approximate commercial Geranium production. During the production of the plants, day temperatures averaged 18° C., night temperatures averaged 16° C. and light levels ranged from 15 kilolux to 100 kilolux. Plants were four months old when the photograph was taken and plants were nine months old when the description was taken. In the detailed description, color references are made to The Royal Horticultural Society Colour Chart, 1995 Edition, except where general terms of ordinary dictionary significance are used.

Botanical classification: *Pelargonium×hortorum* 'Pacshorg'.

Parentage:

*Female, or seed, parent.*—Unnamed proprietary selection of *Pelargonium×hortorum,* not patented.

*Male or pollen parent.*—Unnamed proprietary selection of *Pelargonium×hortorum,* not patented.

Propagation:

*Type.*—By vegetative terminal cuttings.

*Time to initiate roots, summer.*—About 18 days at temperatures of 20° C.

*Time to initiate roots, winter.*—About 22 days at temperatures of 20° C.

*Time to produce a rooted young plant, summer and winter.*—About four weeks at temperatures of 20° C.

*Root description.*—Fine, fibrous; white in color.

*Rooting habit.*—Freely branching; dense.

Plant description:

*Plant/growth habit.*—Compact, upright to rounded plant habit; densely foliated; vigorous growth habit; freely basal branching habit with about 15 lateral branches developing per plant.

*Plant height, to top of umbels.*—About 35 cm.

*Plant height, to top of leaves.*—About 20 cm.

*Plant width.*—About 40 cm.

*Lateral branches.*—Length: About 18 cm. Diameter: About 8 mm. Internode length: About 2.5 cm. Texture: Pubescent. Color: Close to 144A.

Foliage description:

*Arrangement.*—Alternate or opposite; simple.

*Length.*—About 5 cm.

*Width.*—About 8 cm.

*Shape.*—Reniform, rounded.

*Apex.*—Rounded.

*Base.*—Cordate.

*Margin.*—Crenate.

*Venation pattern.*—Palmate.

*Texture, upper and lower surfaces.*—Pubescent; velvety.

*Color.*—Developing and fully expanded leaves, upper surface: Close to 137A; venation, close to 137A. Developing and fully expanded leaves, lower surface: Close to 137C; venation, close to 146B. Zonation pattern: Faint. Location of zone: Towards margin. Width: About 2.5 cm. Color: Close to 147A. Petiole: Length: About 5 cm. Diameter: About 2 mm. Texture, upper and lower surfaces: Pubescent. Color, upper and lower surfaces: Close to 146B.

Flower description:

*Flower arrangement/shape.*—Semi-double rotate flowers arranged in rounded hemispherical umbels arising from apical leaf axils; umbels displayed above the foliage on strong peduncles; depending on the position in the umbel, flowers face upright to outwardly; flowers flat to slightly cupped.

*Fragrance.*—None detected.

*Quantity of flowers.*—Freely flowering habit; about 25 flower umbels develop per plant; each umbel with about 20 flower buds and open flowers.

*Flowering season.*—Year-round under greenhouse conditions; long flowering period, in the garden in Dresden, Germany, flowering is continuous from April until frost in the autumn; plants begin to flower about 75 days after planting.

*Flower longevity.*—Individual flowers last about six to ten days on the plant; umbels last about three to four weeks on the plant; flowers persistent.

*Umbel height.*—About 8 cm.

*Umbel diameter.*—About 13 cm.

*Flower diameter.*—About 5.5 cm.

*Flower depth (height).*—About 2 cm.

*Flower buds.*—Length: About 1 cm. Diameter: About 5 mm. Shape: Shell-shaped. Color: Close to 144A.

*Petals.*—Quantity per flower: About nine; petals imbricate. Length: About 3 cm. Width: About 2.7 cm. Shape: Obovate. Apex: Rounded. Base: Attenuate. Margin: Entire. Texture, upper and lower surfaces: Smooth, glabrous; velvety. Color: When opening and fully opened, upper surface: Darker than 32A; at the base, close to 155D; venation, close to 32A; color does not fade with development. When opening and fully opened, lower surface: Close to 32A; at the base, close to 155D; venation, close to 32A.

*Petaloids.*—Quantity per flower: About three. Length: About 1.5 cm. Width: About 5 mm. Shape: Irregular. Apex: Rounded. Base: Attenuate. Margin: Entire. Texture, upper and lower surfaces: Smooth, glabrous; velvety. Color: When opening and fully opened, upper surface: Darker than 32A; at the base, close to 155D; venation, close to 32A; color does not fade with development. When opening and fully opened, lower surface: Close to 32A; at the base, close to 155D; venation, close to 32A.

*Sepals.*—Quantity per flower: Five arranged in a single whorl. Length: About 1 cm. Width: About 3 mm. Shape: Lanceolate. Apex: Acute. Margin: Entire. Texture, upper and lower surfaces: Smooth. Color, upper and lower surfaces: Close to 144A.

*Peduncle (umbel stem).*—Length: About 15 cm. Diameter: About 4 mm. Strength: Strong. Angle: Mostly erect. Texture: Pubescent. Color: Close to 144A.

*Pedicel (individual flower stem).*—Length: About 4 cm. Diameter: About 2 mm. Strength: Moderately strong; flexible. Texture: Pubescent. Color: Close to 175A.

*Reproductive organs.*—Androecium: Stamen quantity per flower: About ten. Anther length: About 2 mm. Anther shape: Tubular. Anther color: Close to 176A. Pollen amount: Abundant. Pollen color: Close to 169A. Gynoecium: Pistil quantity per flower: One. Pistil length: About 1 cm. Stigma shape: Five to six-parted. Stigma color: Close to 46A. Style length: About 4 mm. Style color: Close to 46A. Ovary color: Close to 139D.

*Seeds.*—Shape: Elliptic. Length: About 3 mm. Diameter: About 1 mm. Color: Close to 165A.

Disease/pest resistance: Plants of the new Zonal Geranium have not been observed to be resistant to pathogens and pests common to Zonal Geraniums.

Garden performance: Plants of the new Zonal Geranium have been observed to tolerate rain, wind and temperatures ranging from about 1° C. to about 35° C. to about 40° C. and have demonstrated good garden performance.

It is claimed:

1. A new and distinct Zonal Geranium plant named 'Pacshorg' as illustrated and described.

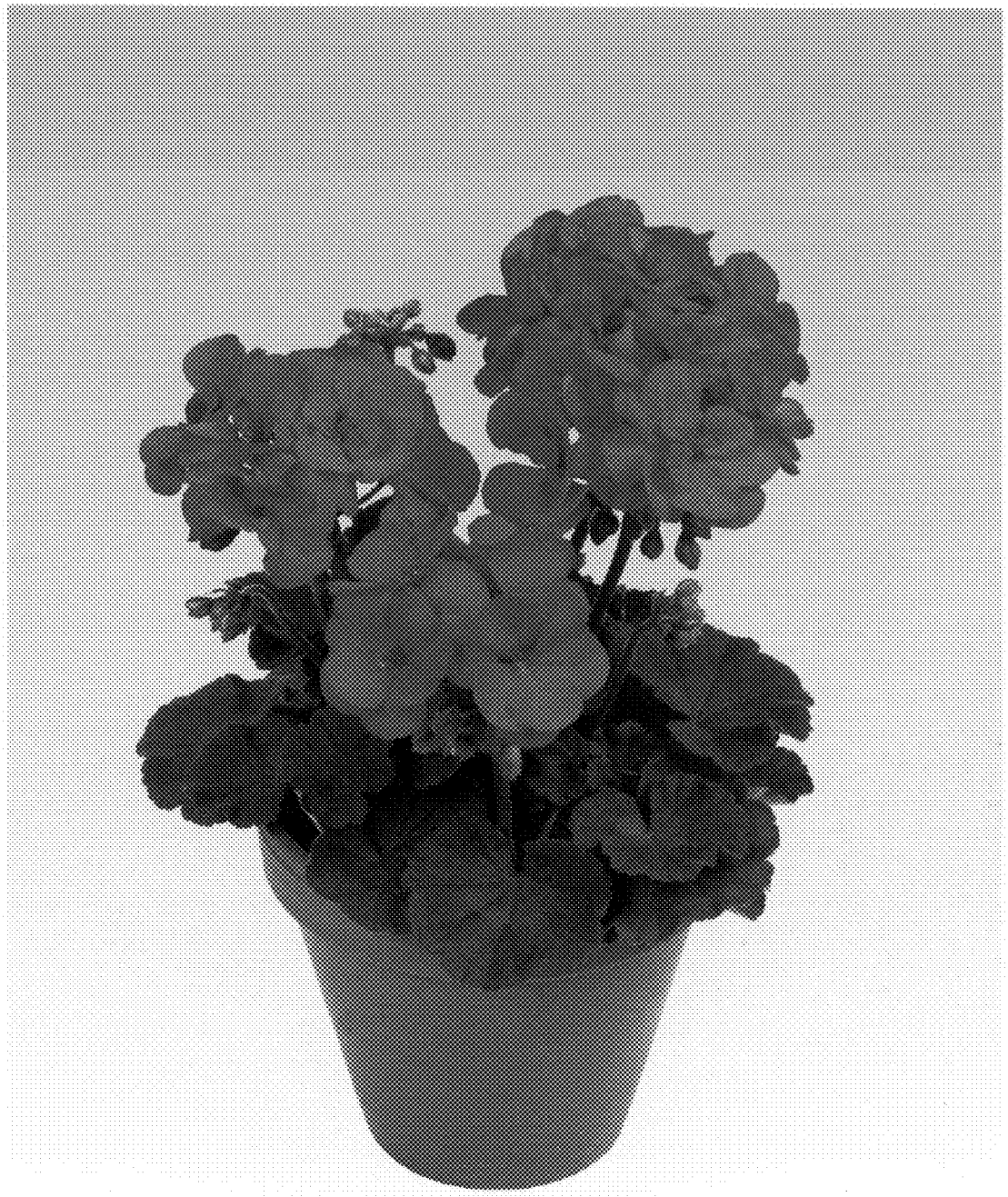

* * * * *